United States Patent
Wang et al.

(10) Patent No.: US 10,493,106 B2
(45) Date of Patent: Dec. 3, 2019

(54) METHOD FOR REMOLDING BONE MARROW MICROENVIRONMENT

(71) Applicant: GUANGZHOU INSTITUTES OF BIOMEDICINE AND HEALTH, CHINESE ACADEMY OF SCIENCES, Guangdong (CN)

(72) Inventors: Jinyong Wang, Guangdong (CN); Chengxiang Xia, Guangdong (CN); Yong Dong, Guangdong (CN); Tongjie Wang, Guangdong (CN); Xiaofei Liu, Guangdong (CN); Juan Du, Guangdong (CN); Yang Geng, Guangdong (CN); Lijuan Liu, Guangdong (CN); Hongling Wu, Guangdong (CN)

(73) Assignee: GUANGZHOU INSTITUTES OF BIOMEDICINE AND HEALTH, CHINESE ACADEMY OF SCIENCES, Guangdong (CN)

( * ) Notice: Subject to any disclaimer, the term of this patent is extended or adjusted under 35 U.S.C. 154(b) by 0 days.

(21) Appl. No.: 15/869,633

(22) Filed: Jan. 12, 2018

(65) Prior Publication Data
US 2019/0111084 A1 Apr. 18, 2019

(30) Foreign Application Priority Data
Oct. 16, 2017 (CN) .......................... 2017 1 0958674

(51) Int. Cl.
*A61K 35/28* (2015.01)
*A61K 9/00* (2006.01)
(Continued)

(52) U.S. Cl.
CPC ............ *A61K 35/28* (2013.01); *A61K 9/0019* (2013.01); *A61P 7/06* (2018.01); *A61P 35/02* (2018.01); *C12N 5/0669* (2013.01)

(58) Field of Classification Search
CPC .... A61K 35/28; A61K 9/0019; C12N 5/0669; A61P 7/06; A61P 35/02
See application file for complete search history.

(56) References Cited

U.S. PATENT DOCUMENTS

| | | | |
|---|---|---|---|
| 2009/0104163 A1* | 4/2009 | Deans ................ | A61K 39/001 424/93.7 |
| 2011/0207166 A1 | 8/2011 | Vaiselbuh | |
| 2015/0238532 A1* | 8/2015 | Frenette ................ | A61K 35/28 424/93.7 |

FOREIGN PATENT DOCUMENTS

| | | |
|---|---|---|
| CN | 1407088 | 4/2003 |
| CN | 102016010 | 4/2011 |
| CN | 104136034 | 11/2014 |

OTHER PUBLICATIONS

Song et al. Mouse bone marrow-derived mesenchymal stem cells inhibit leukemia/lymphoma cell proliferation in vitro and in a mouse model of allogeneic bone marrow transplant. International Journal of Molecular Medicine 36: 139-149, 2015. (Year: 2015).*

(Continued)

*Primary Examiner* — Sean C. Barron
(74) *Attorney, Agent, or Firm* — Workman Nydegger

(57) ABSTRACT

The present invention discloses a method for remolding bone marrow microenvironment in a subject having an impaired bone marrow microenvironment, which comprises implanting a composition comprising isolated mesenchymal stromal cells (MSCs) into the bone marrow cavity of the subject. The method of the present invention successfully remolds the bone marrow microenvironment, recovers the normal hematopoiesis of bone marrow, inhibits/delays the pathological process of leukemia and significantly prolongs the survival period. In addition, the method according to the present invention can be used for the treatment of hemato- (Continued)

logic tumors such as leukemia and aplastic anemia (AA), which is safe and effective but has no side effects.

16 Claims, 8 Drawing Sheets

(51) Int. Cl.
*C12N 5/077* (2010.01)
*A61P 7/06* (2006.01)
*A61P 35/02* (2006.01)

(56) References Cited

OTHER PUBLICATIONS

Tormin et al. CD146 expression on primary nonhematopoietic bone marrow stem cells is correlated with in situ localization. (Blood (2011), v117(19), p. 5067-5077. (Year: 2011).*
Southcott et al. The Expression of Human Blood Group Antigens During Erythropoiesis in a Cell Culture System. Blood (1999), v93(12), p. 4425-4435. (Year: 1999).*
NCBI Gene entry 2994—Glycophorin B (GYPB).*
Yuan, Ya Hong et al., "Intrabone Marrow Injection Enhances Placental Mesenchymal Stem Cell Mediated Support of Hematopoiesis in Mice", *Turkish Journal of Medical Sciences,*, vol. 46, Apr. 3, 2015.
International Search Report cited in PCT/CN2017/108943 dated Jul. 13, 2018.

* cited by examiner

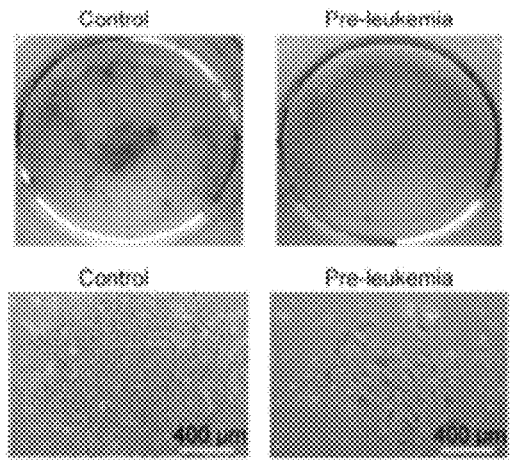
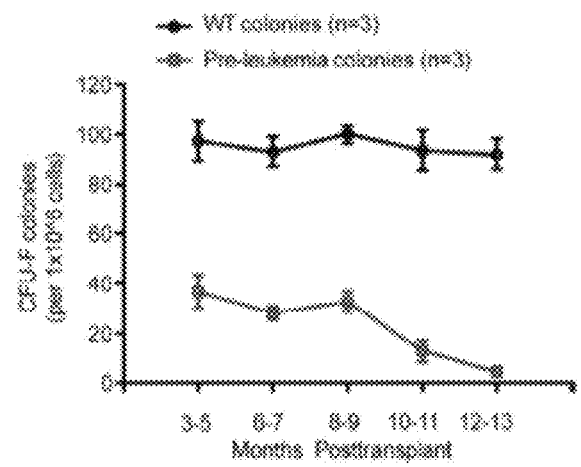
Figure 2A
Figure 2B
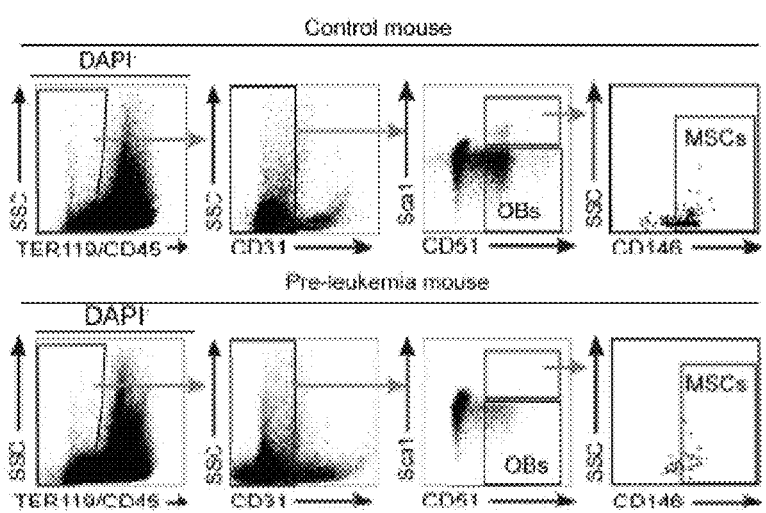
Figure 3A
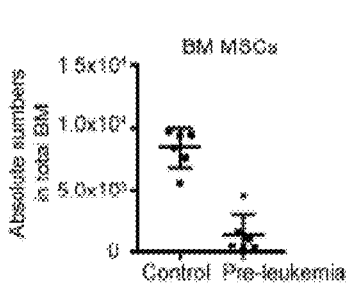
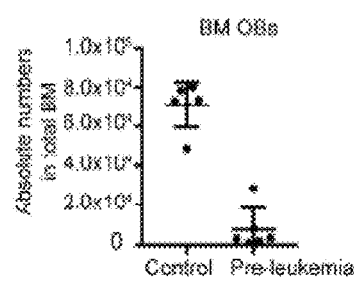
Figure 3B
Figure 3C

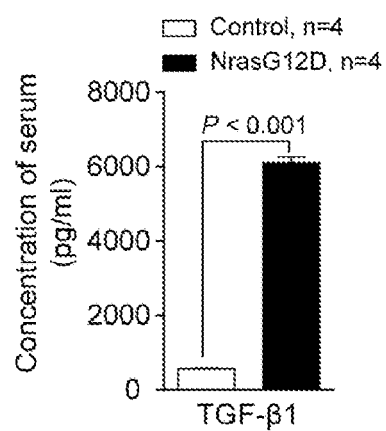 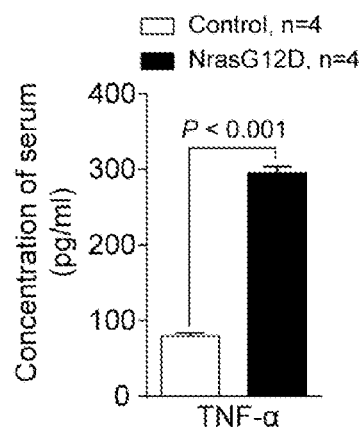 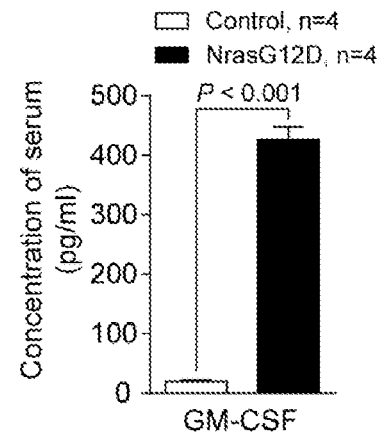
*Fig. 4A*  *Fig. 4B*  *Fig. 4C*
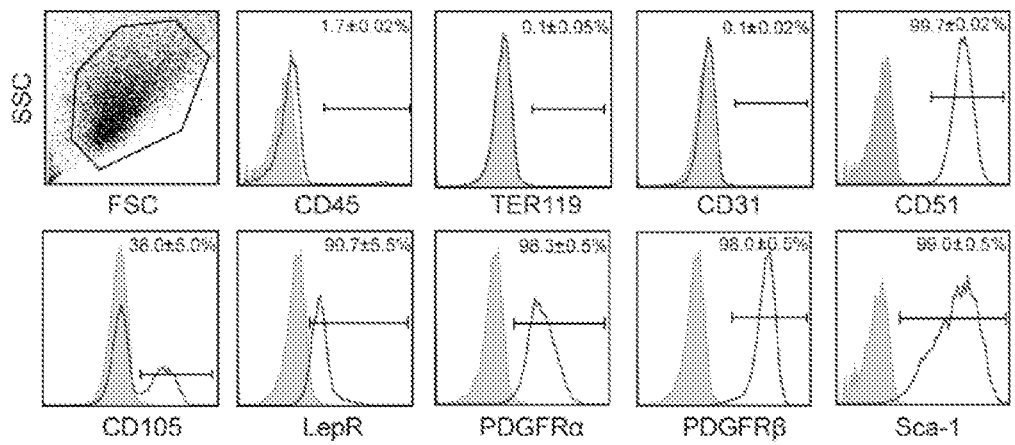
*Fig. 5*
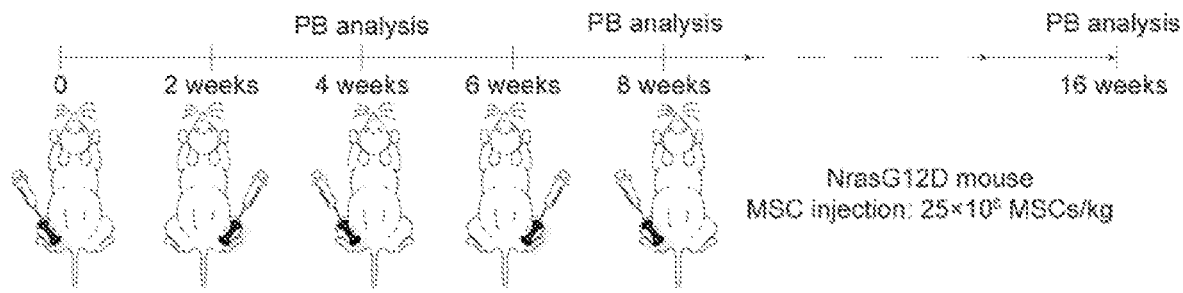
*Fig. 6*

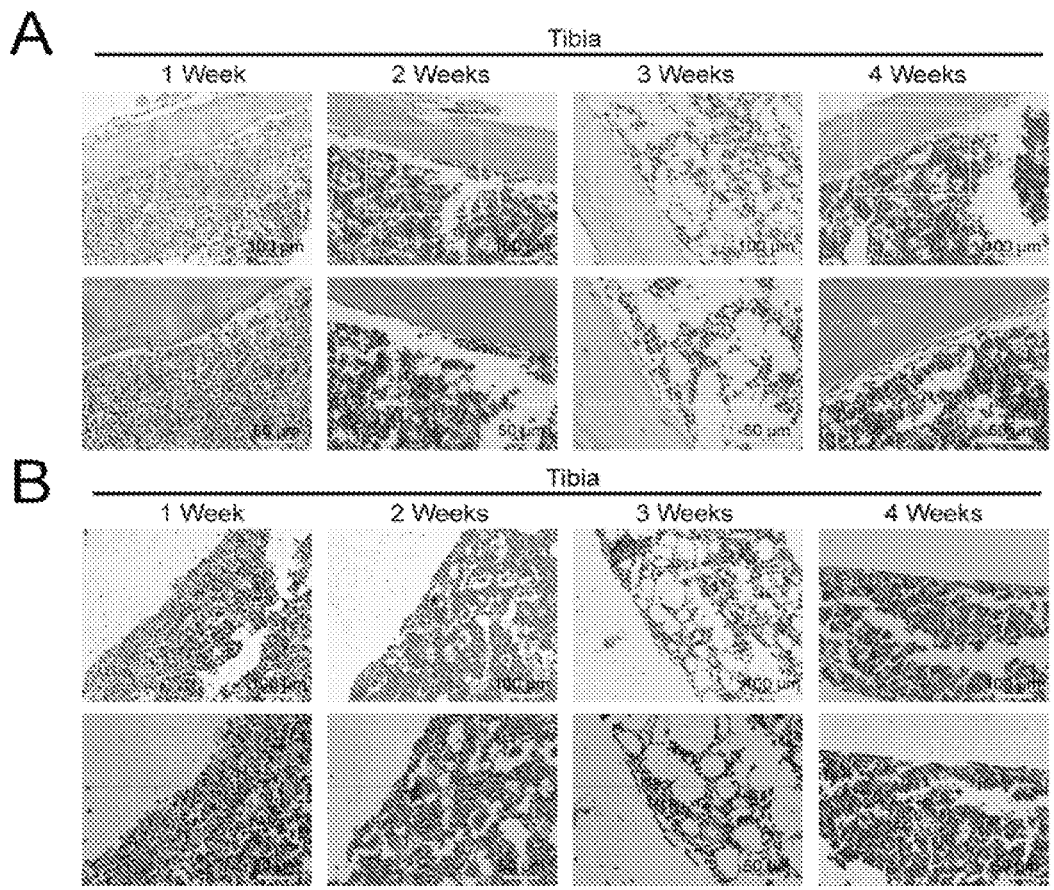
*Fig. 8*
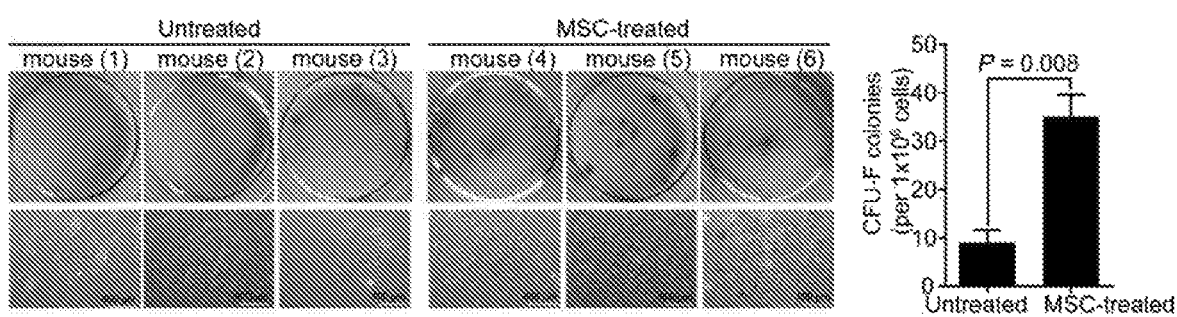
*Fig. 9A*           *Fig. 9B*

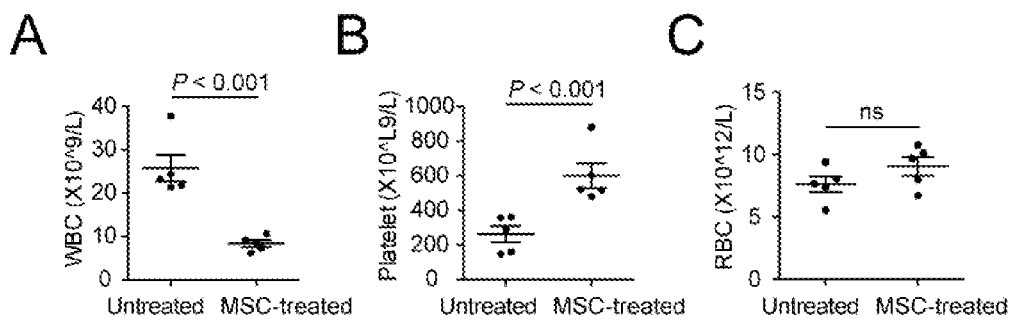
*Fig. 10*
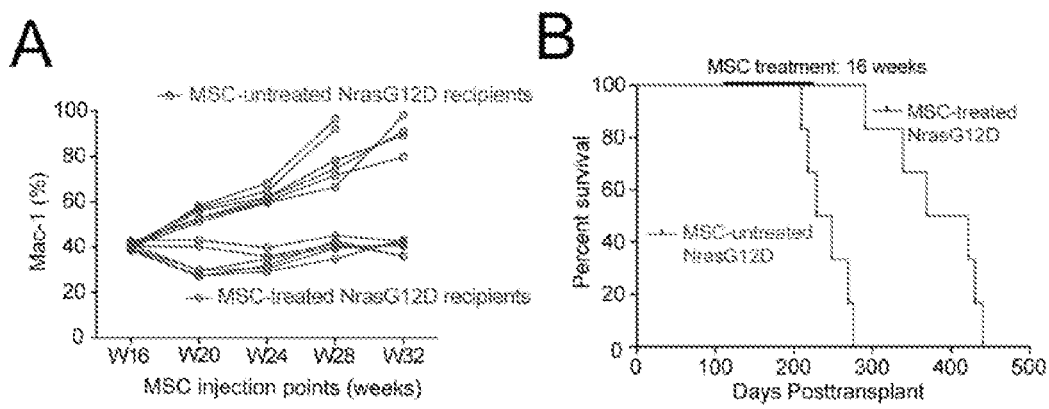
*Fig. 11*
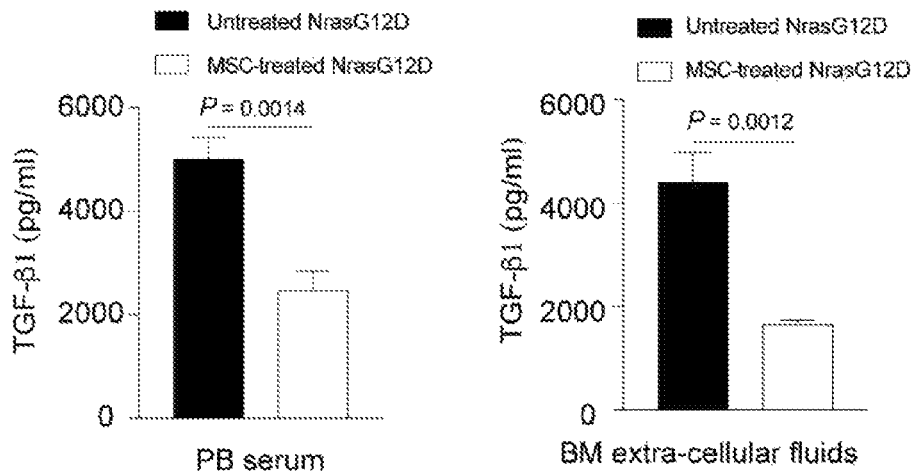
*Fig. 12A*  *Fig. 12B*

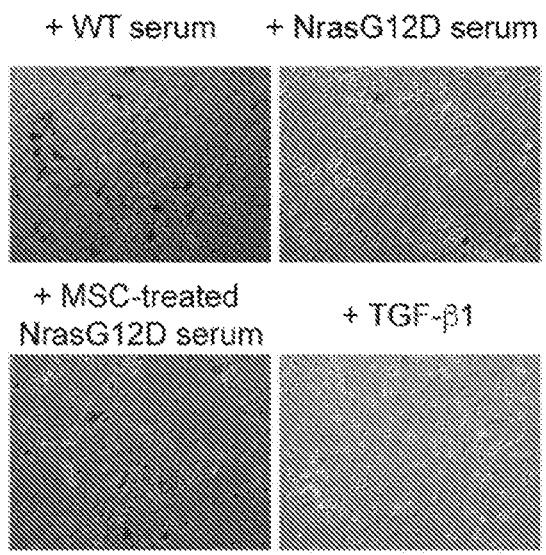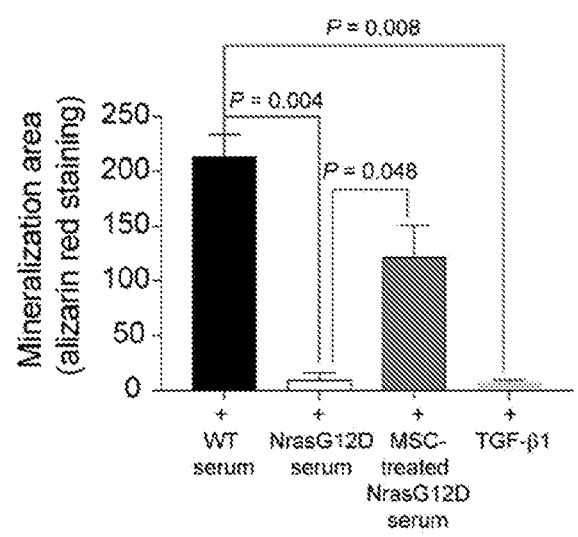
*Fig. 13A*          *Fig. 13B*

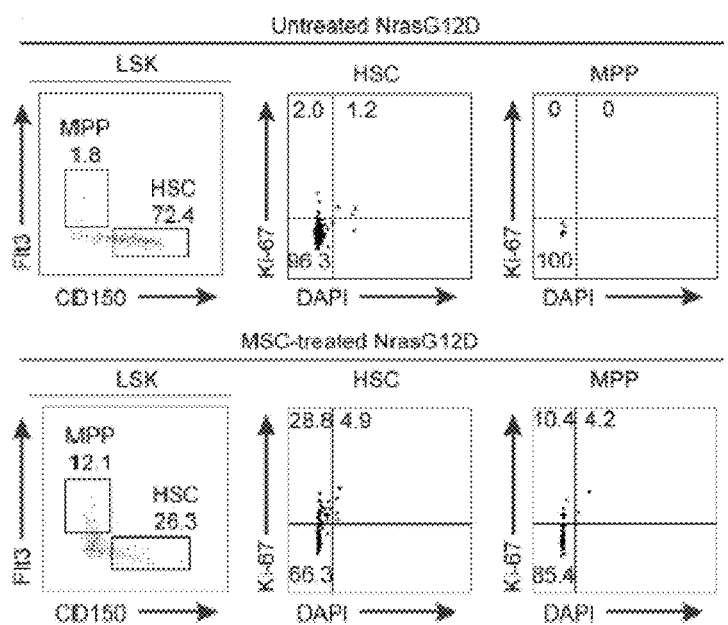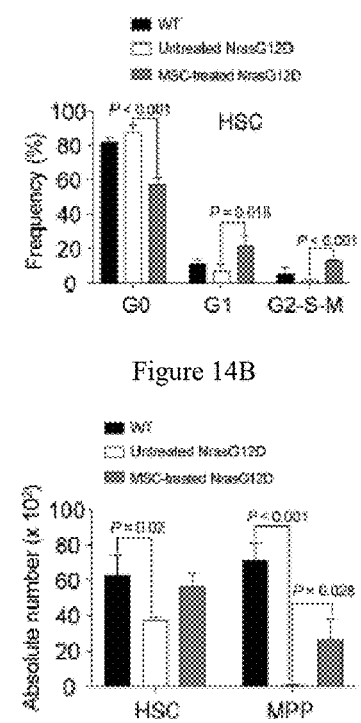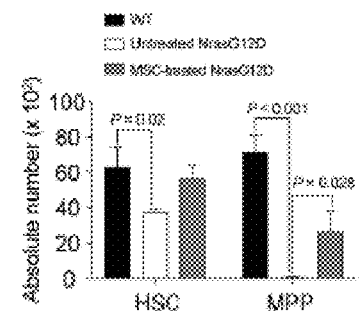
Figure 14A
Figure 14B
Figure 14C
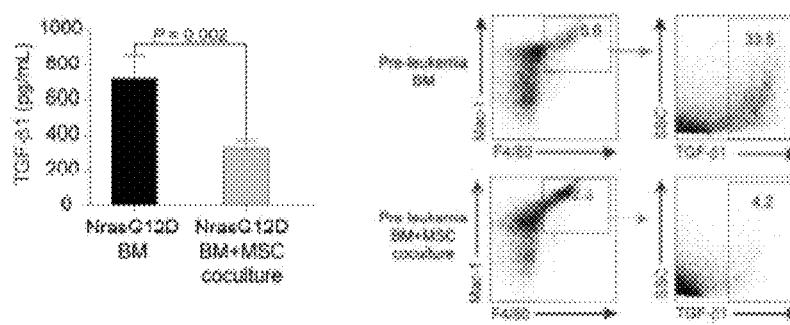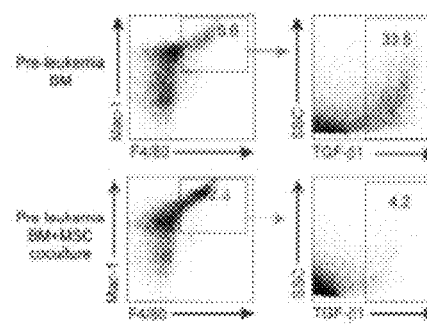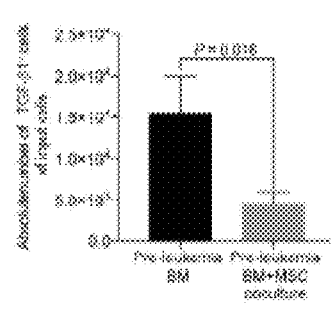
Figure 15A
Figure 15B
Figure 15C

METHOD FOR REMOLDING BONE MARROW MICROENVIRONMENT

TECHNICAL FIELD

The present invention relates to the field of remolding bone marrow microenvironment, in particular, relates to a method for remolding bone marrow microenvironment and application thereof in the treatment of cancer, particularly leukemia.

BACKGROUND

Chronic myelomonocytic leukemia (CMML) and juvenile myelomonocytic leukemia (JMML) are clonal hematologic malignancies characterized by myelodysplastic syndromes (MDS) and myeloproliferative diseases (MPD). CMML and JMML are associated with mutations at carcinogenic sites in genes involved in RAS/MAPK signaling, and 25% to 40% of patients suffering from CMML/JMML have somatic mutations in NRAS gene. It has been reported that a mouse carrying an endogenous mutation of the Nras allele will suffer from a CMML-like disease, which disease has a long latency. It has also been reported that frequent associations between MDS/MPN diseases and the functional disorders of bone marrow (BM) microenvironment have been shown in human patients and animal models that are suffering from CMML/JMML. Aplastic anemia (AA) is a disease mainly characterized by decrease of whole blood cells caused by the failure in hematopoietic function of bone marrow, which is caused in turn by bone marrow hematopoietic stem cell deficiencies, impaired hematopoietic micro-environment and immune mechanism changes due to a variety of factors. The bone marrow microenvironment is a complex network structure with multiple functions, consisting of several types of cells including mesenchymal stromal cells (MSCs), endosteal osteoblasts (OBs), endothelial cells and other rare cell types. The MSCs can be isolated and proliferate in vitro. MSCs are precursor cells of bone marrow stromal cells and account for 0.01% to 0.001% of bone marrow mononuclear cells, equivalent to 1% of the number of HSCs. MSCs can differentiate into osteoblasts, chondrocytes, adipocytes, myocytes, pericytes, reticular fibroblasts and nerve cells among other types under different induction conditions.

At present, MSCs are commonly used in the treatment of systemic graft versus host disease (GVHD) and can improve wound healing and promote the recovery of lung damage, kidney damage and myocardial damage. However, the response to MSCs is not always desirable, and for example, it is known to be affected by the inflammatory state in patients. In addition, MSCs are pluripotent cells and can differentiate into adipocytes, osteoblasts, chondrocytes, myoblasts and/or neuron-like cells after being injected into recipient host. Therefore, it is difficult to predict the exact results of injecting the MSCs into BM microenvironment, such as effects of MSCs injection on the recovery of normal hematopoietic functions, the inhibition of disease progression and other aspects.

At present, the methods for treating hematologic malignancies mainly include chemotherapy, radiotherapy and combined hematopoietic stem cell transplantation. However, the treatment methods described above are accompanied by, in addition to tumor recurrence, varying degrees of side effects including severe damage to non-tumor, healthy cells, especially to germ cells, and graft versus host disease (GVHD) and the like, which seriously affect the life quality of patients. Therefore, there is an urgent need for such treatment methods that can effectively treat the hematologic tumors but have little or even no side effects on patients. The bone marrow microenvironment in patients suffering from hematologic malignancies is usually destructed by the tumor, and thus the normal hematopoiesis of the bone marrow is reduced, or even to failure. In turn, dysfunction/depletion of the bone marrow mesenchymal microenvironment plays a positive role in promoting the progression of pathological deterioration of hematologic malignancies including leukemia, and aplastic anemia. So far, there is no effective way to solve problems in the remolding of pathological bone marrow microenvironment. Therefore, it is very important for the remolding of bone marrow microenvironment under pathological condition and for the remission and treatment of hematologic malignancies to provide a method for remolding bone marrow microenvironment effectively.

SUMMARY OF THE INVENTION

In view of the drawbacks in the prior art, the present invention aims to provide a method for remolding bone marrow microenvironment and application thereof. The method according to the present invention successfully remold the pathological bone marrow microenvironment for the first time, effectively reverse the reduction and failure of the hematopoiesis of bone marrow resulting from, problems such as depletion of bone marrow mesenchymal cells and disappearance of endosteal osteoblasts in bone marrow microenvironment due to the destruction by tumors and the like, successfully recover the normal hematopoiesis of bone marrow microenvironment, and significantly prolong the survival period of the subjects. In addition, the method according to the present invention can be used to treat hematologic tumor and aplastic anemia (AA); preferably, the hematologic tumor is leukemia; further preferably, the hematologic tumor is juvenile myelomonocytic leukemia or chronic myelomonocytic leukemia. The method according to the present invention is safe and effective but has no side effects.

In one aspect, the present invention provides a method for remolding bone marrow microenvironment in a subject having a damaged bone marrow microenvironment, comprising implanting a composition comprising isolated mesenchymal stromal cells (MSCs) into the bone marrow cavity of the subject.

In a particular preferred embodiment, the mesenchymal stromal cells are obtained from the endosteum and/or bone marrow nucleated cells of a healthy subject.

Preferably, the healthy subject is a mammal.

Further preferably, the healthy subject is a mouse. The mesenchymal stromal cells have a phenotype of TER119$^-$CD45$^-$CD31$^-$Sca1$^+$CD51$^+$CD146$^-$ when the subject is a mouse.

Alternatively, the healthy subject is human. The mesenchymal stromal cells have a phenotype of CD235ab$^-$CD45$^-$CD34$^-$CD31$^-$CD271$^+$CD146$^+$ when the subject is human.

In a particular preferred embodiment, the composition comprising isolated mesenchymal stromal cells further comprises pharmaceutically acceptable carriers, diluent or vehicle. Preferably, the pharmaceutically acceptable carrier, diluent or vehicle is phosphate buffer or saline.

In a particular preferred embodiment, the implantation is performed by local injection for multiple times.

In a particular preferred embodiment, the implantation is performed at a dose of $1.0 \times 10^5$ to $3.0 \times 10^7$ MSCs/kg of body weight, preferably $2.5 \times 10^7$ MSCs/kg of body weight.

In a particular preferred embodiment, the implantation is performed once a week, once every two weeks, once every three weeks or once a month. Preferably, the implantation is performed once every two weeks. Preferably, the implantation is performed within a time window of 12 to 24 weeks, preferably 16 weeks.

In a particular preferred embodiment, the subject suffers from disease(s) selected from hematologic tumor and aplastic anemia (AA). Preferably, the hematologic tumor is leukemia. Further preferably, the hematologic tumor is juvenile myelomonocytic leukemia or chronic myelomonocytic leukemia.

In a particular preferred embodiment, the bone marrow microenvironment will exhibit one or more condition(s) selected from recovery of osteoblasts and partial recovery of functional MSCs after implanting the composition comprising isolated mesenchymal stromal cells (MSCs) into the bone marrow cavity of the subject.

In a particular preferred embodiment, the subject will exhibit one or more condition(s) selected from recovery of normal hematopoiesis, inhibition of tumor growth and prolonging of survival period after implanting the composition comprising isolated mesenchymal stromal cells (MSCs) into the bone marrow cavity of the subject.

In a second aspect, the present invention provides use of the method according to the first aspect in the treatment of hematologic tumor and aplastic anemia.

Preferably, the hematologic tumor is leukemia. Further preferably the hematologic tumor is juvenile myelomonocytic leukemia or chronic myelomonocytic leukemia.

Based on the improvement of bone marrow microenvironment under the tumor burden, the present invention develops a method for local intra-osseous injection of bone marrow mesenchymal cells obtained from donors for multi-times, for the first time. The present invention successfully remold the pathological bone marrow microenvironment for the first time, and effectively reverse the reduction and failure of the hematopoiesis of bone marrow resulting from problems such as depletion of bone marrow mesenchymal cells and disappearance of endosteal cells in bone marrow microenvironment due to the destruction by tumors and the like, successfully recover the normal hematopoiesis of bone marrow microenvironment, and significantly prolong the survival period of mice suffering from leukemia. The method according to the present invention which is performed by using stem cells is safe and effective but has no side effects in treating leukemia.

The present invention can successfully reverse the gradual depletion of the bone marrow microenvironment occurring in leukemia mouse models, successfully remold the bone marrow microenvironment, recover the normal hematopoiesis of the bone marrow, inhibit/delay the pathological process of leukemia and significantly prolong the survival period by local intra-osseous implantation of bone marrow mesenchymal cells obtained from donors with the optimized dose and interval time of injection.

DESCRIPTION OF THE DRAWINGS

FIG. 2 are results of the colony forming unit-fibroblast (CFU-F) assay showing the depletion condition of functional MSCs in NrasG12D recipient mice. FIG. 2A shows the Wright Giemsa staining of the CFU-F assay. FIG. 2B shows the dynamic analysis of the CFU-F colonies during the occurrence and development process of leukemia induced by NrasG12D, in which the WT-MSC colonies were obtained from recipient mice receiving transplantation of wild-type bone marrow (WT BM) cells and the NrasG12D-MSC colonies were obtained from recipient mice receiving transplantation of bone marrow cells with NrasG12D mutations.

FIG. 3 shows the numbers of MSCs having a phenotype of TER119$^-$CD45$^-$CD31$^-$CD51$^+$Sca1$^+$CD146$^+$ and osteoblasts (OBs) having a phenotype of TER119$^-$CD45$^-$CD31$^-$CD51$^+$Sca1$^-$ in the bone marrow of NrasG12D mice as detected by flow cytometry. FIG. 3A shows the gate strategy for MSCs and OBs in the flow cytometry detection; the cytometry graphs from a representative WT mouse (upper, as control) and a NrasG12D recipient mouse (lower) were shown in this graph. FIG. 3B shows a statistical result of the absolute number of MSCs in the overall bone marrow nucleated cells. FIG. 3C shows a statistical result of the absolute number of OBs in the overall bone marrow nucleated cells.

FIG. 4 shows that the levels of proinflammatory cytokines in the serum of NrasG12D recipient mice at a pre-leukemic phase were increased. FIG. 4A: TGF-β1, FIG. 4B: TNF-α, FIG. 4C: GM-CSF.

FIG. 5 shows the identification of surface markers on the isolated and cultured MSCs.

FIG. 6 shows the schematic graph of MSCs transplantation experiment performed in the Examples.

FIG. 8 shows results of the hematoxylin-eosin staining (A) and the histochemical staining for osteocalcin (B), showing that the osteoblasts close to endosteum in the NrasG12D recipient mice began to recover at the $3^{th}$ week after the injection of MSCs.

FIG. 9 shows results of the CFU-F assay (FIG. 9A) and the statistical analysis of clones of the CFU-F assay (FIG. 9B, n=4), showing that the functional MSCs in the bone marrow mesenchymal microenvironment were partially recovered after the treatment with MSCs.

FIG. 10 is a statistical analysis showing that the total number of white blood cells was significantly decreased (A), the number of platelet was significantly increased (B) and the total number of erythrocytes showed no significant change (C) in peripheral blood of the NrasG12D recipient mice treated with MSCs.

FIG. 11 shows that the development of leukemia can be successfully inhibited (A) and the survival time of NrasG12D recipient mice can be significantly prolonged (B) by an intervention at early time which is performed by in situ intraosseous injection of MSCs; groups treated with MSCs: n=6, medium value of survival time=395.5 days; untreated groups: n=6, median value of survival time=238.5 days, p<0.0001.

FIG. 12 shows the TGF-β1 levels in serum (FIG. 12A) and bone marrow cavity of mice (FIG. 12B) as detected by ELISA, showing that the TGF-β1 levels in serum and bone marrow cavity of mice treated with MSCs were significantly decreased as compared with those of untreated mice.

FIG. 13 shows the effect of TGF-β1 on the osteogenesis as confirmed by in vitro osteogenic differentiation assay. FIG. 13A shows results of the alizarin red staining after inducing osteogenic differentiation of MSCs for 21 days.

FIG. 13B shows statistical analysis of the area of calcium nodules formed per unit area (n=3).

FIG. 14 shows the cell cycles of HSCs and MPPs (FIG. 14A), the statistical results of cell cycles of HSCs (FIG. 14B), and the statistical analysis of the absolute numbers of HSCs and MPPs (FIG. 14C) in the bone marrow of untreated and MSCs-treated NrasG12D recipient mice.

FIG. 15 shows the level of TGF-β1 in the supernatant of in vitro co-cultured cells as detected by ELISA (FIG. 15A), and the statistical analysis of TGF-β1 level in co-cultured cells (FIG. 15B) and the level of TGF-β1 secreted by Mac1$^+$F4/80$^+$ NrasG12D tumor cells (FIG. 15C) as detected by intracellular flow cytometry staining.

DETAILED DESCRIPTION

Figure 1A:
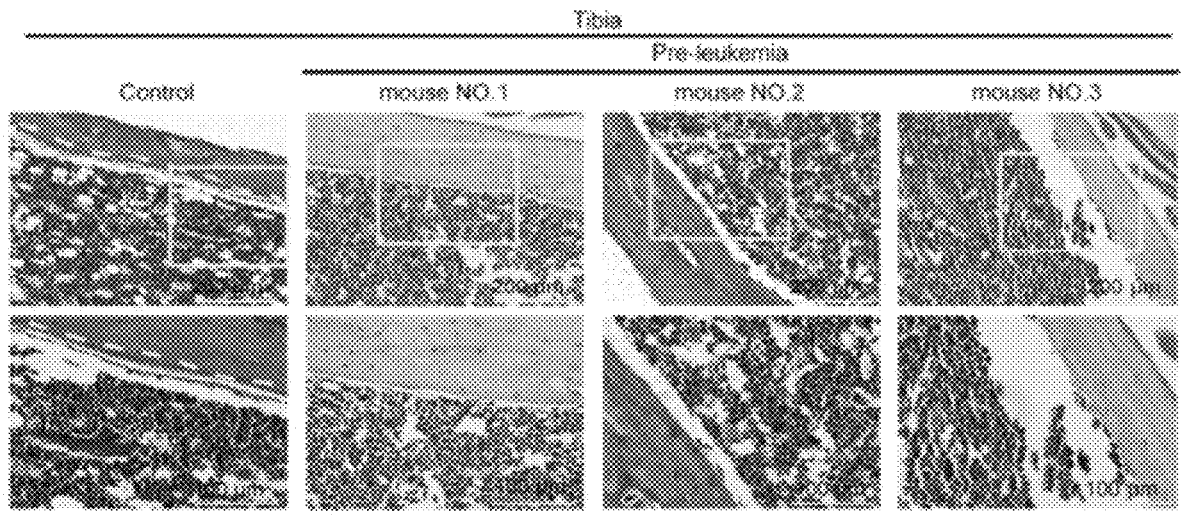
FIG. 1 shows results of the hematoxylin-eosin staining (FIG. 1A) and the histochemical staining for osteocalcin (FIG. 1B) for tibias of the representative control mice and the NrasG12D recipient mice in a pre-leukemic phase.

Examples are listed below for better understanding of the present invention. It will be apparent to those skilled in the art that the examples are only illustrative of the invention and should not be construed as particular limitation of the invention.

Term Definition

The term "bone marrow microenvironment" as used herein refers to cell components composed of supporting cells adjacent to hematopoietic stem cells in bone marrow and involving in the maintenance, self-renewal and directed differentiation of the hematopoietic stem cells. The bone marrow microenvironment herein mainly refers to bone marrow-derived mesenchymal stromal cells and the osteoblasts close to endosteum.

The term "mesenchymal stromal cells" as used herein refers to a kind of stromal cells that support the hematopoietic stem cells in bone marrow and are capable of secreting a variety of factors to support hematopoiesis.

The term "endosteum" as used herein refers to a membrane tissue that grows adherent to the medial side of the bone.

The term "NrasG12D recipient mouse" and "NrasG12D leukemia mouse" as used herein can be used interchangeably and both refer to a CMML/JMML-like mouse model which is constructed by introducing a NrasG12D mutation. The construction method is described in detail in example 1.

General Method

Immunohistochemical Staining of Bone Sections

For hematoxylin & eosin staining, tibia and femur bones from control mice and NrasG12D recipient mice were fixed with 4% paraformaldehyde and then treated for histological hematoxylin & eosin staining (in a pathology lab, GIBH).

For osteocalcin staining, after being dehydrated by 30% sucrose, the tibia was decalcified in 14% EDTA, and then embedded into paraffin for slicing (in a pathology lab, GIBH). The activity of endogenous peroxidase was quenched and blocked by blocking buffer (5% normal goat serum and 0.3% Triton X-100 in PBS). The slides were incubated at 4° C. overnight with the associated primary rabbit anti-mouse polyclonal antibody, followed by incubation at room temperature for 1 hour with secondary biotinylated anti-rabbit antibody (goat anti-rabbit IgG-HRP, sc-2004, Santa Cruz, 1:1000 diluted). The following primary antibody was used: anti-osteocalcin polyclonal antibody (ab93876, Abcam, 1:500). The antigens were visualized by using a mixture of DAB substrate and DAB chromogen. The slides were counterstained with hematoxylin and then sealed with neutral gum. Images were captured and processed by using the Motic Digital Slice Scanning System (VMV1 VMDPCS, Motic) and DSS Scanner software.

Fibroblast Colony Forming Units (CFU-F) Assay

One million of BM nucleated cells were seeded into a 6-well plate and cultured in complete MesenCult™ medium (Catalog 05512, StemCell Technology) for 10-14 days. The BM cells were incubated in a humidified chamber at 37° C. at 5% $CO_2$ and half of the medium was changed on day 7. Giemsa staining was performed as described in Yang D, Zhang X, Dong Y, et al. Enforced expression of Hoxa 5 in haematopoi nervous stem cells leads to aberrant erythropoiesis in vivo. *Cell Cycle.* 2015; 14 (4): 612-620.

Analysis and Sorting by Flow Cytometry

Analysis of hematopoietic lineage for peripheral blood (50 μl) and bone marrow was performed by using flow cytometry as described in Wang J, Liu Y, Li Z, et al. Endogenous oncogenic Nras mutation initiates hematopoietic malignancies in a dose- and cell type-dependent manner. *Blood.* 2011; 118(2):368-379. The following antibodies which can conjugate directly with surface antigens were used: FITC-CD45.2 (104), APC-Thy1.2 (53-2.1), biotin-CD3 (145-2C11), biotin-CD3 (RM4-5), biotin-CD8 (53-6.7), PE-CD19 (1D3), PE-Cy7-Mac1 (M1/70) and APC-Gr-1 (RB6-8C5), and the antibodies were purchased from eBiosciences.

For intracellular staining of cytokines, cells were collected and stained with antibodies against surface antigens including PerCP-Cy5.5-Mac1 (M1/70)/APC-Mac1 (M1/70), biotin-G1 (RB6-8C5), PE-Ly6C HK1.4), APC-eFluor 780-F4/80 (BM8) and streptavidin-PE, which were purchased from eBiosciences. Cells were fixed and permeabilized (Cytofix/Cytoperm, BD Biosciences) and then intracellular staining was performed by using PerCP-Cy5.5-TGF-β1 (TW7-16B4, Biolegend).

Cell cycle analysis was performed as described in Wang J, Liu Y, Li Z, et al. Endogenous oncogenic Nras mutation initiates hematopoietic malignancies in a dose- and cell type-dependent manner. *Blood.* 2011; 118(2):368-379. Briefly, lineage markers (CD3, CD4, CD8, CD19, B220, TER119, Gr1, Mac1, CD48) were stained with antibodies conjugated with FITC for the cell cycle analysis of HSCs/MPPs. Cell staining was also performed with APC-eFluor 780-cKit (2B8), PerCP-Cy5.5-Sca1 (D7), PE-Cy7-CD150 (TC15-12F12.2), PE-Flt3 (A2F10). After washing, cells were fixed with 4% PFA. Finally, the fixed cells were permeabilized with 0.1% saponin in PBS and stained with APC-Ki67 (SolA15, eBioscience), followed by staining with DAPI (Invitrogen).

The identification and sorting of MSCs were performed by isolating the BM cells through washing the tibia and femur with DPBS containing 2% FBS, and then cutting the bones into small pieces and digesting them with 1 mg/ml collagenase II in a shaking incubator at 37° C. for 1-2 hours. The cells collected from endosteum and bone marrow were mixed together and filtered with a 70 μm cell filter. For the identification and sorting of MSCs, cells were stained with the antibodies including APC-780E-CD45 (30-F11), APC-eFluor 780-Ter119 (TER-119), PE-Cy7-Sca-1 (D7), biotin-CD51 (RMV-7) and streptavidin-PE, which were purchased from eBiosciences, and APC-CD31 (MEC13.3) and PerCP-Cy5.5-CD146 (ME-9F1), which were purchased from Biolegend. The method for straining was described in Yang D, Zhang X, Dong Y, et al. Enforced expression of Hoxa5 in haematopoietic stem cells leads to aberrant erythropoiesis in vivo. *Cell Cycle.* 2015; 14(4):612-620.

The stained cells were analyzed on FACS Calibur or LSR Fortessa (BD Bioscience) and MSCs was sorted by using AriaII (BD Bioscience) for RNA sequencing and then analyzed by using FlowJ software (FlowJo).

ELISA Assay

Serum samples were collected from peripheral bloods of the NrasG12D recipient mice and the control mice. Extracellular liquid samples of the bone marrow were collected from bone marrow of the NrasG12D recipient mice and the control mice. The concentrations of cytokines (TGF-β1, TNF-α, GM-CSF) were detected by using an Enzyme-Linked Immunosorbent Assay (ELISA) Kit (4A Biotechnology Corporation, Beijing, China) according to the manufacturer's instructions.

Osteogenic Differentiation Assay

The MSCs were seeded into growth medium in a 6-well plate which has been pre-coated with gelatin solution at a density of $2\times10^4$ cells/cm$^2$ and cultured in a humidified incubator at 37° C. at 5% $CO_2$. When cells reached about 60-70% confluence, the growth medium was removed and 2 mL of Mouse Mesenchymal Stem Cell Osteogenic Differentiation Medium (MUBMX-90021, Cyagen) was added. The medium was changed every three days. Peripheral serum (10 μL/mL) from wild-type, untreated and MSCs-treated NrasG12D leukemia mice and 5 ng/mL TGF-β1 were added to the induction medium, respectively, throughout the osteogenic differentiation assay. After induction for 3 weeks, the cells were fixed with 4% neutral formaldehyde and stained with alizarin red. Images were captured and the area of the formed calcium nodules was calculated by Image-Pro software.

Co-Culture of MSCs & BMNCs

GFP-labeled MSCs were seeded in a 6-well plate at a density of $1\times10^5$ cells/well. CD45$^+$ BMNCs were sorted from the NrasG12D recipient mice and seeded into 2 ml of α-MEM+10% FBS+50 ng/ml SCF medium at a density of $1\times10^6$ cells/ml. MSCs and CD45$^+$ cells were co-cultured at 37° C. at 5% $CO_2$. Next day, 1 ml fresh medium was added. After culturing for 7 days, TGF-β1 level in the culture supernatant was measured by ELISA, and the cell source of TGF-β1 was detected by flow cytometry.

EXAMPLES

Example 1 Establishment of Leukemia Mouse Models (CMML/JMML-Like) with Their Bone Marrow Microenvironment Being Progressively Destructed Leukocytes from mice with NrasG12D mutation (LSL NrasG12D/+; Vav-Cre) or control mice (CD45.2) (with removal of stromal cells) were transplanted into CD45.1 recipient mice subjected to a sub-lethal dose of radiation (6.5 Gy) via retrobulbar vein to establish chronic myelomonocytic leukemia-like (CMML/JMML-like) mouse models. Tumor burden and hyperplasia of tumor cells in the peripheral blood were detected and analyzed by flow cytometry. In the mouse model of leukemia induced by NrasG12D, different development stages of leukemia were defined according to the ratio of myeloid cells in peripheral blood of the mice. It is called Pre-leukemic phase (hereinafter referred to as "PL phase" for short sometimes) when the ratio of myeloid cells (Mac1) in the peripheral blood of mice is more than 20% and less than 60%, and Leukemic phase when the Mac1>60%.

Figure 1B:
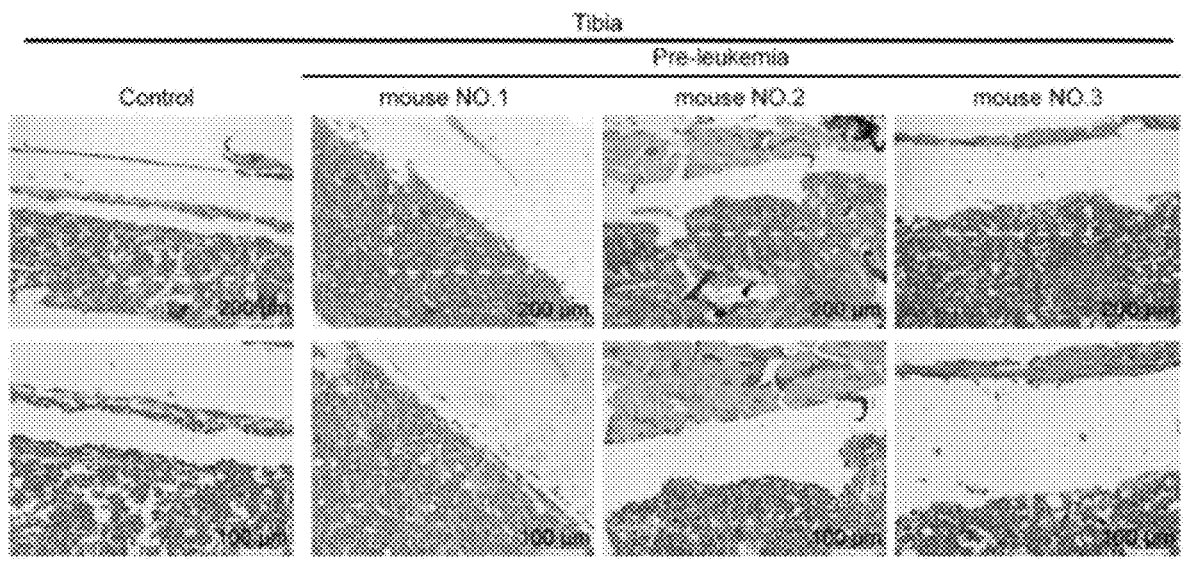
Figure 7:
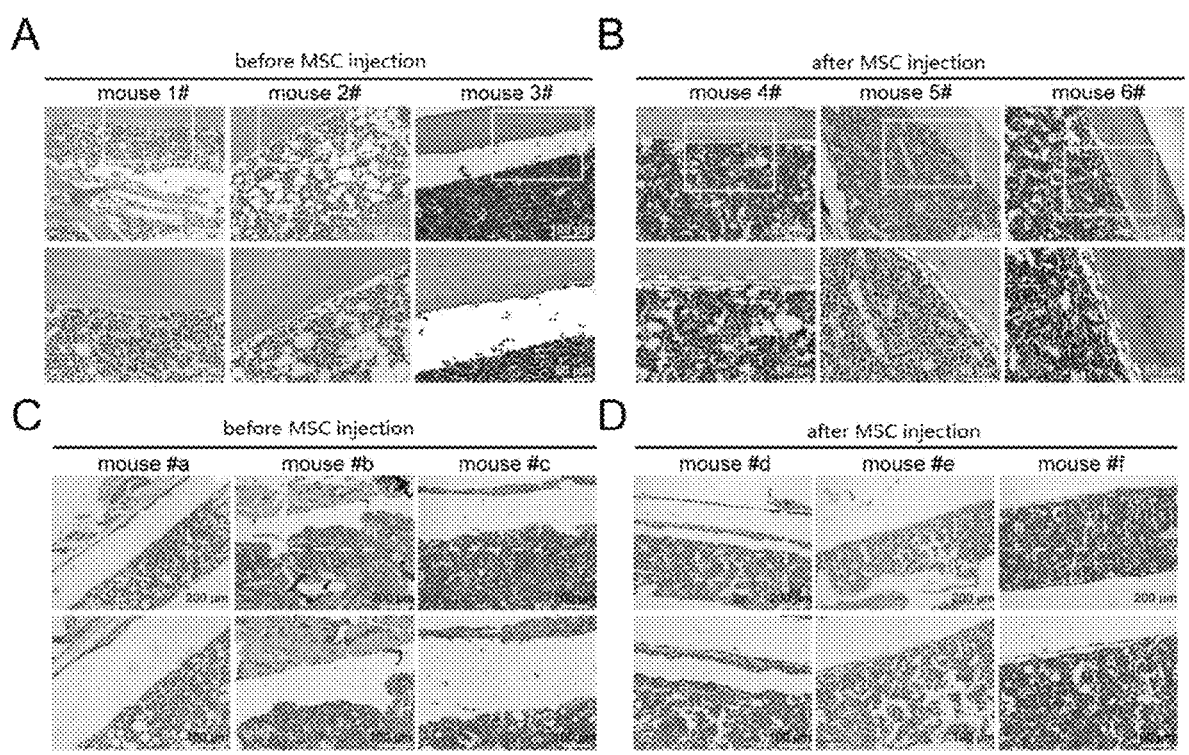
FIG. 7 shows results of the hematoxylin-eosin staining (A and B) and the histochemical staining for osteocalcin (C and D), showing that the osteoblasts close to endosteum in the NrasG12D recipient mice were recovered in part after the injection of MSCs.

Example 2 The Histological Analysis Demonstrated that the Endosteal Osteoblasts were Gradually Depleted in Bone Marrow Microenvironment During Pre-Leukemic Phase In order to study whether bone marrow mesenchymal microenvironment was depleted gradually during the pre-leukemic phase of leukemia induced by NrasG12D, firstly the control mice and NrasG12D recipient mice in a pre-leukemic phase were sacrificed and tibias and femurs were isolated. The tibias and femurs were then fixed with 4% paraformaldehyde, followed by hematoxylin-eosin straining and immunohistochemical staining for osteocalcin. The result of hematoxylin-eosin staining (FIG. 1A) showed that osteoblasts (hereinafter referred to as "OBs" for short sometimes) close to endosteum in the NrasG12D recipient mice in a pre-leukemic phase were already depleted. The result of histochemical staining for osteocalcin (FIG. 1B) showed that osteoblasts close to endosteum in the NrasG12D recipient mice in the pre-leukemic phase were already depleted. That is, histological staining of the tibias demonstrated that the osteoblasts close to endosteum almost disappeared during the pre-leukemic phase.

Example 3 The Cytological Analysis Demonstrated that Mesenchymal Stromal Cells (MSCs) in the Bone Marrow Microenvironment were Depleted Gradually with the Development and Progression of Leukemia A fibroblast colony forming unit (CFU-F) assay was performed to assess the depletion condition of functional mesenchymal stromal cells in the NrasG12D recipient mice. Firstly, bone marrow nucleated cells (BMNCs) were isolated under sterile conditions after sacrificing the mice, and $1\times10^6$ BMNCs from each mouse of three groups were suspended with 2 mL MesenCult™ complete medium (Catalog 05512, StemCell Technology) and seeded in a single well of a six-well plate, respectively. Cells were cultured in a cell incubator at 37° C. at 5% $CO_2$ till the 7th day, at which time point half of the culture medium was changed and then cells were cultured for another 3 to 7 days. At the 10$^{th}$ to 14$^{th}$ day of the culture, cells were fixed with pre-cooled ethanol and were stained with Giessa Sima, and the number and size of the formed clones were counted (FIG. 2A). It was observed that the functional MSCs were decreased and depleted gradually during the pre-leukemic phase (FIG. 2B).

Example 4 The Flow Cytometry Assay Demonstrated that the Bone Marrow Microenvironment was Depleted Gradually with the Development and Progression of Leukemia The numbers of MSCs having a phenotype of TER119$^-$CD45$^-$CD31$^-$CD51$^+$Sca1$^+$CD146$^+$ and OBs having a phenotype of TER119$^-$CD45$^-$CD31$^-$CD51$^+$Sca1$^-$ in the bone marrow of NrasG12D mice were further analyzed by flow cytometry. Firstly, bone marrow cells were flushed out from the tibias and femurs by using 5 mL DPBS containing 2% FBS to collect bone marrow nucleated cells. Nucleated cells in the endosteum were collected by cutting the compact bones into small bone pieces and digesting the same with 1 mg/ml type II collagenase in a shaking incubator at 37° C. for 1-2 hours. Nucleated cells from the bone marrow and the endosteum were mixed and filtered through a 70 micron cell screen and then 1 mL ACK red cell lysate was added (the ACK red cell lysate was prepared by mixing 8.02 g $NH_4Cl$ (150 mM), 1.00 g $KHCO_3$ (10 mM), 0.37 g $Na_2EDTA$ (0.1 mM) and 800 ml $H_2O$, adjusting the pH value to 7.2-7.4 with 1 N HCl, adding water to a volume of 1 L, and finally filtering the mixture through a 0.22 μm filter to remove bacteria, and stored at room temperature for use) to lyse the red blood cells, followed by centrifugation (4° C., 500 g, 5 min), and 5 times volume of DPBS+2% FBS was added to resuspend the cells, followed by centrifugation. Cells were resuspended with 500 μl DPBS+2% FBS and CD16/32 (1:200) antibody was added to incubate for 15 min on ice, and then anti-CD51-biotin (RMV-7) antibody was added to incubate for 15 min on ice. 5× volume of DPBS+2% FBS was added, followed by centrifugation, and then cells were resuspended with 500 μL DPBS+2% FBS and were added by the antibodies (1:200) including anti-CD45-APC/eFluor® 780 (30-F11), anti-Ter119-APC/eFluor® 780 (TER-119), anti-Sca-1-PE/Cy7 (D7), anti-CD31-APC (MEC13.3), anti-CD146-PerCP/Cy5.5 (ME-9F1) to incubate on ice for 15 min. 5× volumes of DPBS+2% FBS was added, followed by centrifugation, and cells were resuspended with DPBS+2% FBS containing DAPI (1:400). Stained cells were analyzed by LSR Fortessa (BD Bioscience) and the resulting data was analyzed by using a FlowJ software (FlowJo) (FIG. 3A). The statistical analysis showed that the numbers of MSCs and OBs with the respective phenotypes were decreased gradually with the development and progression of leukemia (FIGS. 3B and 3C).

Example 5 The Systemic Inflammation in the NrasG12D Recipient was Increased During the Pre-Leukemic Phase We determined the pro-inflammatory cytokines including TGF-β1, TNF-α and GM-CSF in the serum of NrasG12D recipient mice in a pre-leukemic phase. The result showed that the levels of TGF-β1, TNF-α and GM-CSF were significantly increased (FIGS. 4A-C).

Example 6 Isolation, In Vitro Culture and Phenotype Identification of the Bone Marrow Mesenchymal Stromal Cells MSCs transplantation experiments were performed to investigate whether the MSCs could help in remolding the destructed bone marrow mesenchymal microenvironment. Mesenchymal stromal cells isolated from the endosteum and bone marrow from 4-weeks-old wild-type mice were used in our MSCs transplantation experiments. Firstly, the bone marrow was blown out from the bone cavity, and the bones were cut into small pieces of bones and digested with 1 mg/ml of type II collagenase at 37° C. for 1-2 hours. The digested bone pieces were washed and spread into a 6 cm dish, and then 6 mL MSC complete medium (A-MEM+10% FBS) was added for culturing to obtain MSCs derived from culture of bone tissues. Bone marrow was blown with FBS suspension to obtain a suspension of bone marrow nucleated cells, and subsequently, the MSCs therein were labeled by straining (TER119$^-$CD45$^-$CD31$^-$Sca1$^+$CD51$^+$CD146$^+$), and then sorted directly into a MSC medium to obtain MSCs derived from sorting of bone marrow. MSCs derived from culture of bone tissues and MSCs derived from sorting of bone marrow were mixed together for culturing, and then subjected to washing and changing the medium on the third day before continuing to culture. After culturing for 5 days, the bone pieces were removed. After washing, the adherent cells were collected by digesting with 0.25% (wt/vol) trypsin and then passaged at a ratio of 1:3, with the medium being changed every 48 hours. The isolated and cultured MSCs were collected and identified for their phenotypes (CD45, TER119, CD31, CD51, CD105, LepR, PDGFRα, PDGFRβ, Sca-1, shown in FIG. 5) by using flow cytometry before injection. All MSCs used for injection were cells cultured to the third generation.

Example 7 A Method for Local Intraosseous Injection of MSCs

MSCs transplantation experiments were performed by intraosseous injection according to the procedure shown in FIG. 6. Cells were suspended in 20 μl of DPBS+2% FBS and injected into the tibias of leukemia mice induced by NrasG12D through a method of in situ intraosseous injection at a dose of $2.5 \times 10^7$ MSCs/kg of body weight. The injection was performed once every two weeks for a total of 16 weeks. Tibias on each side were treated discontinuously by switching the injection site, and the peripheral blood of the treated mice was detected by flow cytometry every month to track changes in tumor burden to allow the surgical trauma to recover as far as possible.

Example 8 Treatment of Leukemia Mouse Models Induced by NrasG12D Through Local Intraosseous Injection of MSCs Successfully Recovered the Osteoblasts in Bone Marrow Microenvironment The leg bones of NrasG12D leukemia mice treated with MSCs injection were subjected to hematoxylin-eosin staining and immunohistochemical staining for osteocalcin to determine whether there were regenerated endosteal osteoblasts in NrasG12D leukemia mice which have been subjected to MSCs transplantation treatment. The results showed that endosteal osteoblasts were observed along the medial side of the tibias of mice which had been treated with MSCs (FIGS. 7A-D).

A dynamic staining analysis was further performed for the tibias of NrasG12D leukemia mice treated with MSCs. The results showed that regenerated osteoblasts began to appear in the endosteum at the $3^{th}$ week after the first MSCs injection, and the number of regenerated osteoblasts was increased significantly at the $4^{th}$ week (FIGS. 8A and 8B).

However, the inventors found in further experiments that the tumor burden was not reduced by intraosseous injection of MSCs isolated from the NrasG12D leukemia mice in a pre-leukemic phase (data not shown).

Example 9 Treatment of Leukemia Mouse Models Induced by NrasG12D Through Local Intraosseous Injection of MSCs Successfully Recovered the Mesenchymal Stromal Cells in Bone Marrow Microenvironment NrasG12D leukemia mice subjected to in situ MSCs treatment were sacrificed, and the bone marrow nucleated cells BMNCs thereof were isolated firstly and then subjected to a CFU-F experiment and a statistical analysis (FIGS. 9A and 9B) to analyze the functional MSCs in bone marrow mesenchymal microenvironment of NrasG12D leukemia mice being treated with MSCs. The results showed that BMNCs in the bone marrow of MSCs-treated NrasG12D leukemia mice formed more CFU-F colonies compared to the untreated NrasG12D leukemia mice, suggesting that the functional MSCs in the bone marrow mesenchymal microenvironment at the injection site was recovered in part.

Example 10 Treatment of Leukemia Mice Induced by NrasG12D Through Local Intraosseous Injection of MSCs Successfully Recovered the Normal Hematopoiesis The blood cell count was performed for NrasG12D leukemia mice which had been treated with MSCs as described above. The results showed that the number of WBCs in peripheral blood of NrasG12D leukemia mice treated with MSCs was significantly decreased (p<0.001), while the platelet level was significantly increased (p<0.001) (FIGS. 10A-C), indicating that the normal hematopoiesis can be recovered in part by remolding bone marrow microenvironment.

Example 11 Local Intraosseous Injection of MSCs Can Successfully Inhibit the Tumor Growth and Prolong the Survival Period MSCs interventional treatment was performed on mice during the pre-leukemic phase (Mac1$^+$%<60% in peripheral blood). The results showed that the numbers of myeloid cells in peripheral blood of all NrasG12D leukemia mice in the control group without MSCs interventional treatment were increased continuously and all these mice were died within 36 weeks. However, the numbers of myeloid cells in peripheral blood of the NrasG12D leukemia mice which had been treated with MSCs did not continue to increase (FIG. 11A). Moreover, the survival time of NrasG12D leukemia mice which had been subjected to MSCs interventional treatment at early time (median of survival time=395.5 days) was longer than that of control mice without being subjected to MSCs intervention (median of survival time=238.5 days) (FIG. 11B), which suggested that the MSCs intervention allows NrasG12D leukemia mice to survive for a long time in the tumor-bearing condition.

Example 12 Local Intraosseous Injection of MSCs Promoted the Remolding of Bone Marrow Mesenchymal Microenvironment by Reducing the Level of TGF-β1

TGF-β1 has a negative regulatory effect on osteogenesis. Therefore, the following experiments were carried out to study whether local intraosseous injection of MSCs can promote the regeneration of endosteal osteoblasts by regulating the level of TGF-β1. Firstly, TGF-β1 levels in the serum and the bone marrow cavity of the treated mice were measured by ELISA; and meanwhile, bone marrow sections of the NrasG12D leukemia mice were immunohistochemically stained for osteocalcin by a histochemical method. Results of both experiments showed that TGF-β1 levels in the serum and the bone marrow cavity of the MSCs-treated NrasG12D leukemia mice were significantly decreased compared to the untreated control mice (see FIGS. 12A and 12B).

In vitro osteogenic differentiation assay was then carried out to verify the effect of TGF-β1 on osteogenesis. Serum from the untreated NrasG12D leukemia mice, serum from the MSCs-treated NrasG12D leukemia mice and individual TGF-β1 factor were continuously added, respectively, during the process of inducing osteogenic differentiation of wild-type MSCs. After 21 days of osteogenic differentiation, the cells were fixed with 4% neutral formaldehyde and then stained with alizarin red solution. The area of the calcium nodules formed per unit area were calculated and compared. The results showed that the inhibitory effect of serum from the untreated NrasG12D leukemia mice on osteogenic differentiation was stronger than that of serum from the MSCs-treated NrasG12D leukemia mice, and the individual TGF-β1 factor also showed a strong inhibitory effect on osteogenic differentiation (see FIGS. 13A and 13B), suggesting that local intraosseous injection of MSCs may promote the regeneration of endosteal osteoblasts by reducing the level of TGF-β1.

Example 13 Local Intraosseous Injection of MSCs Activated the HSCs in a Dormant State by Reducing the Level of TGF-β1 to Promote Recovery of the Normal Hematopoiesis High level of TGF-β1 promotes HSCs to enter into a dormant state. Therefore, cell cycle analysis by flow cytometry (Ki-67 and DAPI) was performed on HSCs in the bone marrow of the untreated and MSCs-treated NrasG12D leukemia mice to study whether local intraosseous injection of MSCs can promote recovery of the normal hematopoiesis by regulating TGF-β1 level. The results showed that the proportion of HSCs at the mitotic stage in the bone marrow of MSCs-treated NrasG12D recipient mice was significantly increased compared to the untreated NrasG12D recipient mice, and the absolute number of MPP cells was significantly increased (See FIGS. 14A, 14B and 14C), all of which suggested that local intraosseous injection of MSCs may activate the HSCs in a dormant stage to enter an active cell cycle by reducing the level of TGF-β1, and thus promote recovery of the normal hematopoiesis.

Example 14 MSCs Regulated the Level of TGF-β1 Secreted by Mac1$^+$F4/80$^+$ NrasG12D Tumor Cells In vitro co-culture experiments were designed to study the action mode of MSCs regulating the secretion of TGF-β1 by NrasG12D tumor cells. Firstly, MSCs derived from the bone marrow of GFP mice were isolated and seeded into a six-well plate at a density of 1×10$^5$ MSCs/well. The CD45$^+$ cells in bone marrow of NrasG12D recipient mice were then sorted and resuspended in a co-cultured complete culture (α-MEM+10% FBS+50 ng/μl SCF) at a density of 1×10$^6$ cells/ml, and then cultured alone or co-cultured with MSCs respectively. The culture medium was supplemented with 1 ml complete medium every other day. After culturing in a cell incubator at 37° C. for 7 days, TGF-β1 level in the supernatant of the culture was measured by ELISA, and the intracellular level of TGF-β1 of the co-cultured cells was measured by flow cytometry. The results showed that the TGF-β1 level in the supernatant of the group co-cultured with MSCs was significantly lower than that in the supernatant of the group where NrasG12D tumor cells were cultured alone (FIG. 15A). At the same time, the detection results of intracellular flow cytometry showed that TGF-β1 was secreted mainly by Mac1$^+$F4/80$^+$ NrasG12D tumor cells (FIGS. 15B and 15C), which suggested that MSCs regulated the secretion level of TGF-β1 by Mac1$^+$F4/80$^+$ NrasG12D tumor cells.

The invention claimed is:
1. A method for remolding bone marrow microenvironment in a subject suffering from a disease selected from juvenile myelomonocytic leukemia and chronic myelomonocytic leukemia, comprising in situ injecting a composition comprising isolated mesenchymal stromal cells (MSCs) into a bone marrow cavity of the subject, and the composition treating the disease.
2. The method according to claim 1, wherein the mesenchymal stromal cells are obtained from the endosteum and/or bone marrow nucleated cells of a healthy subject.

3. The method according to claim 2, wherein the healthy subject is a mouse; and in this case, the mesenchymal stromal cells have a phenotype of TER119$^-$CD45$^-$CD31$^-$Sca1$^+$CD51$^+$CD146$^+$.

4. The method according to claim 2, wherein the healthy subject is human; and in this case, the mesenchymal stromal cells have a phenotype of CD235ab$^-$CD45$^-$CD34$^-$CD31$^-$CD271$^+$CD146$^+$.

5. The method according to claim 1, wherein the composition comprising isolated mesenchymal stromal cells further comprises pharmaceutically acceptable carriers, diluent or vehicle.

6. The method according to claim 5, wherein the pharmaceutically acceptable carrier, diluent or vehicle is phosphate buffer or saline.

7. The method according to claim 1, wherein the implantation is performed by local injection for multiple times.

8. The method according to claim 1, wherein the implantation is performed at a dose of $1.0 \times 10^5$ to $3.0 \times 10^7$ MSCs/kg of body weight.

9. The method according to claim 1, wherein the implantation is performed at a dose of $2.5 \times 10^7$ MSCs/kg of body weight.

10. The method according to claim 1, wherein the implantation is performed once a week, once every two weeks, once every three weeks or once a month.

11. The method according to claim 1, wherein the implantation is performed within a time window of 12 to 24 weeks.

12. The method according to claim 1, wherein the implantation is performed within a time window of 16 weeks.

13. The method according to claim 1, wherein the disease is juvenile myelomonocytic leukemia.

14. The method according to claim 1, wherein the disease is chronic myelomonocytic leukemia.

15. The method according to claim 1, wherein the bone marrow microenvironment will exhibit one or more condition(s) selected from recovery of osteoblasts and partial recovery of functional MSCs after implanting the composition comprising isolated mesenchymal stromal cells (MSCs) into the bone marrow cavity of the subject.

16. The method according to claim 1, wherein the subject will exhibit one or more condition(s) selected from recovery of normal hematopoiesis, inhibition of tumor growth and prolonging of survival period after implanting the composition comprising isolated mesenchymal stromal cells (MSCs) into the bone marrow cavity of the subject.

* * * * *